United States Patent [19]

McKay

[11] Patent Number: 5,645,084
[45] Date of Patent: Jul. 8, 1997

[54] METHOD FOR SPINAL FUSION WITHOUT DECORTICATION

[75] Inventor: William F. McKay, Memphis, Tenn.

[73] Assignee: Danek Medical, Inc., Memphis, Tenn.

[21] Appl. No.: 482,038

[22] Filed: Jun. 7, 1995

[51] Int. Cl.⁶ .................................................. A61B 19/00
[52] U.S. Cl. ............................ 128/898; 435/69.1; 606/76
[58] Field of Search ................................ 606/60, 61, 72, 606/76; 128/898, 899

[56] References Cited

U.S. PATENT DOCUMENTS

| | | | |
|---|---|---|---|
| 4,294,753 | 10/1981 | Urist | 260/112 |
| 4,526,909 | 7/1985 | Urist | 523/115 |
| 4,619,989 | 10/1986 | Urist | 530/417 |
| 4,761,471 | 8/1988 | Urist | 530/350 |
| 4,789,732 | 12/1988 | Urist | 530/350 |
| 4,857,456 | 8/1989 | Urist | 435/7 |
| 4,877,864 | 10/1989 | Wang et al. | 530/324 |
| 5,013,649 | 5/1991 | Wang et al. | 435/69.1 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,168,050 | 12/1992 | Hammonds, Jr. et al. | 435/69.1 |
| 5,187,076 | 2/1993 | Wozney et al. | 435/69.1 |
| 5,208,219 | 5/1993 | Ogawa et al. | 514/12 |
| 5,318,898 | 6/1994 | Israel | 435/69.1 |
| 5,366,875 | 11/1994 | Wozney et al. | 435/69.1 |
| 5,443,483 | 8/1995 | Kirsch | 606/76 |
| 5,492,697 | 2/1996 | Boyan et al. | 424/422 |
| 5,514,180 | 5/1996 | Heggeness et al. | 606/60 |
| 5,520,923 | 5/1996 | Tija et al. | 424/426 |

FOREIGN PATENT DOCUMENTS

| | | |
|---|---|---|
| WO91/18098 | 11/1991 | WIPO . |
| WO93/00432 | 1/1993 | WIPO . |
| WO94/26892 | 11/1994 | WIPO . |
| WO94/26893 | 11/1994 | WIPO . |

OTHER PUBLICATIONS

*Is it Necessary to Decorticate Segmentally Instrumented Spines to Achieve Fusion?* Ishikawa, Shin, Bowen, Cummings, SPINE, vol. 19, No. 15, pp. 1686–1690.

*Experimental Spinal Fusion With Recombinant Human Bone Morphogenetic Protein–2*, Schimandle, Boden, Hutton, SPINE, vol. 20, No. 12, pp. 1326–1337.

Allen, B.L. Jr.; Ferguson, R.L., In Luque Er, ed., *Segmental Spinal Instrumentation*, New Jersey, Charles B. Slack, Inc., 1984, pp. 185–200.

*Iliac Crest Versus Spinous Process Grafts in Postraumatic Spinal Fusions*, SPINE, vol. 17, No. 7, pp. 790–794, 1992.

Goldthwaite, Noel; White, Arthur H., *Lumbar Spine Surgery*, C.V. Mosby Company, 1987, pp. 512–523.

*Primary Examiner*—Michael Buiz
*Assistant Examiner*—Mark S. Leonardo
*Attorney, Agent, or Firm*—Woodard, Enhardt, Naughton Moriarty & McNett

[57] ABSTRACT

Surgical procedures for stabilizing a spine include exposing a portion of each of adjacent vertebrae requiring fusion and placing an osteoinductive material within an area between the portions of the adjacent vertebrae in contact with the cortical bone of the portions. In another aspect, surgical procedures for stabilizing a spine are provided which include exposing a portion of each of adjacent vertebrae requiring fusion, adding an osteoinductive cytokine to a carrier material and placing the carrier material between the portions of the adjacent vertebrae in contact with the cortical bone of the portions.

28 Claims, No Drawings

METHOD FOR SPINAL FUSION WITHOUT DECORTICATION

FIELD OF THE INVENTION

The present invention broadly concerns spinal fusions. More specifically the invention concerns surgical procedures which employ osteoinductive cytokines and do not require decortication.

BACKGROUND OF THE INVENTION

Spinal fusion is indicated to provide stabilization of the spinal column for disorders such as structural deformity, traumatic instability, degenerative instability, and post resection iatrogenic instability. Fusion, or arthrodesis, is achieved by the formation of an osseous bridge between adjacent motion segments. This is accomplished either anteriorly between contiguous vertebral bodies or posteriorly between consecutive transverse processes, laminae or other posterior aspects of the vertebrae.

Typically, the osseous bridge, or fusion mass, is biologically produced by recreating conditions of skeletal injury along a "fusion site" and allowing the normal bone healing response to occur. This biologic environment at a proposed fusion site requires the presence of osteogenic or osteopotential cells, adequate blood supply, sufficient inflammatory response, and appropriate preparation of local bone.

Under conventional wisdom, it has been generally understood that decortication is required to prepare the bone to increase the likelihood of fusion. Decortication is the processing of removing the outer cortex of spinal bone with a burr to induce bleeding bone and release of its bone marrow contents. Decortication also initiates the inflammatory response, releases osteoinductive cytokines, provides additional osteogenic cells, and creates a host attachment site for the subsequent fusion mass. However, decortication increases blood loss, operative exposure, operative time, post operative pain and the chance of neurological damage. According to a recent study, decortication was deemed essential for fusions without segmental instrumentation although it may not be necessary for fusions with internal fixation. (Ishikawa, Spine: 1686-1690, 1994.)

Bone graft materials are often used to promote spinal fusions. Although autogenous iliac crest cortico-cancellous bone is presently the most successful bone grafting material, the rate of fusion mass consolidation with use of autograft is limited by the rate of normal biologic bone repair. Autograft also requires an additional surgery which increases the risk of infection and may reduce structural integrity at the donor site. Furthermore, many patients complain of significant pain for several years after the surgery. These disadvantages have led to the investigation of bioactive substances that regulate the complex cascade of cellular events of bone repair, such as bone morphogenic protein, for use as alternative or adjunctive graft materials. Bone morphogenic protein (BMP), an osteoinductive cytokine extracted from bone matrix, is capable of inducing bone formation when implanted in a fracture or surgical bone site. BMP actually refers to a group of bone morphogenic proteins belong to the TGF-β super family. The structures of eleven proteins, BMP-1 through BMP-11 have been elucidated. Recombinantly produced human bone morphogenetic protein-2 (rhBMP-2) has been demonstrated in several animal models to be effective in regenerating bone in skeletal defects.

The following events are thought to occur when the BMPs are applied to a bony site: Osteogenic and chondrogenic precursor cells accumulate, cartilage forms and matures, and vascularization occurs during bone formation. As bone formation proceeds, the cartilage and carrier are resorbed. The final result is the restoration of bone and bone marrow in the defect site. The purification of bovine bone-derived bone-inductive protein (Wang et al. 1988) led to the cloning of recombinant human (rh) BMP-2 through rhBMP-8 (Wozney et al. 1988; Wozney 1989; Celeste et al. 1990; Celeste et al. 1992). BMP-2 through BMP-8 are related proteins with several common characteristics. Each BMP is synthesized in a precursor form, with a hydrophobic secretory leader sequence and a substantial propeptide region. The mature protein consists of a dimer of the carboxy-terminal portion of the propeptide molecule. All of the mature regions of these rhBMPs contain one or more N-linked glycosylation sites and seven cysteine residues. The locations of the cysteine residues are conserved within all members of this gene family. The BMPs are proving useful in spinal surgeries in promoting bone healing.

In spite of these developments in bone graft materials, conventional wisdom still maintains that decortication of the fusion site is essential to complete osteoinduction and osteogenesis. Consequently, the above-mentioned drawbacks and risks remain in many fusion procedure, whether or not instrumented with fixation implants. A need has remained for surgical spinal procedures which do not require decortication.

SUMMARY OF THE INVENTION

Briefly describing one aspect of the present invention, there is provided a surgical procedure for stabilizing a spine utilizing an osteoinductive material. According to the procedure, a portion of each of adjacent vertebrae requiring fusion is exposed and the osteoinductive material is placed within an area between the portions of the adjacent vertebrae in contact with the cortical bone of the portions. This procedure is conducted without decortication of any portion of the vertebrae.

In another aspect, surgical procedures for stabilizing a spine are provided which include exposing a portion of each of adjacent vertebrae requiring fusion, adding an osteoinductive cytokine to a carrier material and placing the carrier material between the portions of the adjacent vertebrae in contact with the cortical bone of the portions.

In one embodiment, the osteoinductive cytokine is a bone morphogenic protein, such as BMP-2. The carrier material can be an open-celled polylactic acid polymer, provided in sheets or strips that can be easily placed at the fusion site.

In one aspect of the surgical procedure, the osteoinductive material is placed between posterior aspects of adjacent vertebrae. In a similar manner, the material can be situated within the intradiscal space in direct contact with the vertebral endplates. In either case, the bone cortex remains intact.

It is an object of the invention to provide surgical procedures for stabilizing the spine in which decortication is not necessary. This and other objects, advantages and features are accomplished according to the compositions and methods of the following description of the preferred embodiment of the present invention.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides surgical procedures for stabilizing the spine which do not require decortication. The procedures include exposing a portion of each of the adjacent vertebrae requiring fusion and placing an osteoinductive material within an area between the portions of the adjacent vertebrae in contact with the cortical bone of the portions. This invention is advantageous because it does not require decortication or internal fixation. Decortication, or the removal of the dense outer surface of bone, reduces the bone to bleeding bone. The disadvantages of decortication have led to investigations as to whether decortication is necessary to promote bone healing in fusions and other surgical procedures.

Until the discovery that led to the present invention, decortication was deemed necessary for all procedures without internal fixation. This invention is based upon the surprising discovery that the application of an osteoinductive material within an area between portions of adjacent vertebrae to be fused leads to a stable fusion without internal fixation. This is beneficial because there are risks associated with the use of spinal fixation devices. The profile of the implant may cause complications. Such devices have also been known to fracture, corrode or loosen over time. Radiologists also complain of interference in MRI and X-rays. Therefore, this invention is advantageous because it provides fusions without both decortication and internal fixation.

In another embodiment, the invention provides a surgical procedure for stabilizing a spine which includes the steps of: exposing a portion of each of the adjacent vertebrae requiring fusion; adding an osteoinductive cytokine to a carrier material; and placing the carrier material between the portions of the adjacent vertebrae in contact with the cortical bone of the portions. It is contemplated that the cytokine may be injected into the carrier material either before or after the placing step- It is understood that the step of exposing the portions of the adjacent vertebrae that will ultimately become the fusion site, can be conducted according to known surgical techniques.

The procedures of this invention are contemplated for spinal fusions and other surgical procedures. Preferably, the portions of the adjacent vertebrae to be fused are at the posterior aspect of the spine. The portions are most preferably within the neural arch, such as the transverse processes of the adjacent vertebrae. The material is also most preferably placed bilaterally so that fusion is achieved on both sides of the vertebrae, leading to a more stable fusion. It is contemplated that any number of adjacent vertebrae could be fused according to the methods of this invention. Preferably, the number of vertebrae would be two or three.

It is also contemplated that the portions are the end plates of the adjacent vertebrae. In other words, the placing step would include placing the osteoinductive material into the disc space between adjacent vertebrae. The means of placing the osteoinductive material into the disc space will depend on the medium which contains the osteoinductive cytokine. If the cytokine is suspended or disolved in a liquid medium, the osteoinductive material can be injected directly into the disc space. In such cases, the nucleus pulposus would be removed without decortication.

The osteoinductive material on this invention includes an osteoinductive cytokine. Preferably, the osteoinductive material is a bone morphogenic protein (BMP). Most preferably, the borne morphogenic protein is a BMP-2, such as recombinant human BMP-2. However, any bone morphogenic protein is contemplated including bone morphogenetic proteins designated as BMP-1 through BMP-11. BMPs are commercially available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. The BMP may be provided in freeze-dried powder form and reconstituted intra-operatively in sterile water for injection. Preferably, the sterile water would be supplemented with a buffer vehicle solution as is well known in the art.

It is preferred that the osteoinductive material include an osteoinductive cytokine in a carrier or matrix. The purpose of the carrier component is to retain the osteoinductive component at the site of implantation, prevent soft tissue prolapse into the defect area and enable bony vascular ingrowth to occur during BMP induced bone formation. The choice of matrix material is based on biocompatibility, biodegradability, mechanical properties and interface properties. The particular application of the compositions of the invention will define the appropriate formulation. The carrier may be any suitable carrier capable of delivering the proteins to the site of bone injury- Most preferably, the carrier is capable of being resorbed into the body. Such matrices may be formed of materials presently in use for other implanted medical applications. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalciumphosphate (TCP), hydroxyapatite (HA), biphasic TCP/HA ceramic, polylactic acids and polyanhydrides. Other potential materials are biodegradable and biologically well defined, such as bone or dermal collagen. Further matrices are comprised of pure proteins or extracellular matrix components. The osteoinductive material may also be an admixture of the osteoinductive cytokine and a polymeric acrylic ester carrier. The polymeric acrylic ester can be polymethylmethacrylic.

The osteoinductive material may also be placed in a metal cage fusion device which is implanted in the intervertebral space. Such devices are well known in the art. One such device is disclosed in U.S. Pat. No. 5,397,364 to Kozak et al.

The carriers are preferably provided in strips or sheets which may be folded to the size of the area between the portions of the vertebrae to be fused, or to conform to the fusion site.

This invention applies to any spinal surgical procedure which requires decortication. The application of osteoinductive materials such as BMPs obviate the need for decortication leading to safer surgical procedures. Benefits of this invention will be provided with surgical procedures that employ internal fixation or fusion implants. However, such devices are not required according to the methods of this invention. Surgical procedures which are well known in the art can be safely and conveniently modified according to the invention.

In order to promote a further understanding and appreciation of the invention, the following specific Examples are provided. It will be understood that these examples are illustrative and not limiting in nature.

EXAMPLE 1

OPLA Carrier

Materials and Methods: The need for decortication when using rhSMP-2 with an OPLA carrier was evaluated. Fusion rates of decorticated and undecorticated vertebrae after insertion of a rhBMP-2OPLA implant were evaluated in a single level postevaluated spinal fusion model. Isolated L4-L5 transverse process fusions were evaluated in twenty mature female beagles. The posterior elements were exposed through a limited posterior incision. In the undecorticated group, osteoinductive implants were placed abutting the transverse processes bilaterally without disruption of cortical integrity. In the other group, the transverse processes and apophyseal joints were decorticated with a power burr prior to insertion of implants. The implants consisted solely of rhBMP-2 delivered by an open-cell polylactic acid polymer. Open Porosity Polylactic Acid Polymer (OPLA) was provided in sterile packaged 12.0 mm×6.5 mm×30 mm strips (two strips per package). The pure OPLA was sterilized via gamma irradiation. The rhBMP-2 was provided in freeze-dried powder form and reconstituted intraoperatively in sterile water for injection and supplemented with a buffer vehicle solution. The rhBMP-2 was introduced into the carrier material at the time of surgery by the surgeon. Three doses of rhBMP-2 were used:

| dose of rhBMP-2* | number of animals undecorticated | decorticated |
|---|---|---|
| 920 µg | 3 | 3 |
| 230 µg | 3 | 4 |
| 58 µg | 3 | 4 |

*Dose sequence is logarithmic ($Log_4$)

No internal fixation nor autogenous bone was used in this study. A prior study demonstrated that both autologous iliac crest bone graft and OPLA alone failed to produce transverse process fusion in this model by 3 months. The canines were sacrificed 3 months postoperatively and the lumbar spines (L2-S1) were explanted. Following removal of all soft tissue, the entire motion segment of L4-L5 was removed by transversely cutting thru the L3-L4 disc and the L5-L6 disc. The explanted spines were analyzed by Faxitron™ imaging, computerized tomography (CT), and by manual motion testing. Seven specimens were reserved for histologic evaluation and the remainder were subjected to nondestructive mechanical testing. Stiffness measures were calculated from pure moments and torques applied, in consecutive trials, to the isolated fusion segment in sagittal, coronal, and axial planes. Median values for each plane of motion were analyzed. Data from two specimens (decorticated, 230 µg, 920 µg) were excluded due to apparatus errors.

In preparation for non-destructive testing, the end plates of the L4-L5 functional unit was cleaned of soft tissue and exposed. A transverse hole was drilled through each of the vertebral bodies and a pin was placed into this hole for rigid fixation to the test fixtures. The pin was attached to a plus shaped frame for ease in determining orientation, a hole was drilled dorsal-caudal through the mid substance of the vertebral body. The arm extensions of the frame were aligned with the flexion-extension and lateral bending axes. Eye hooks were located in the ends of the arm extensions to apply pure bending or torsional loads to the unsupported segment of the functional unit through a cable-pulley arrangement. Equal loads were applied to both of the opposing arms using dead weights or appropriate force handle. The maximum load and hence maximum moment or torque of 50 newtons was determined from preliminary biomechanical tests on non treated and treated spines to insure that the level of 50 newtons applied was within the non-destructive range and would allow complete elastic recovery of the functional unit. The vertical displacement of the free end of the functional unit was measured using a Linear Variable Differential Transformer (LVDT).

Using the Faxitron® machine, a high resolution radiograph was taken of each explanted lumbar spine following the removal of soft tissues. (Film: Kodak Industrex Film, 50-13×18 cm, #507-2392, exposure ~30 MA @3 min) This provided a high resolution radiograph which enabled characterization of fusion remodeling including recorticalization of the fusion mass. CT scans were taken at one month, and at sacrifice (3 months) on the explanted lumbar spinal segments, and then were qualitatively and quantitatively analyzed. Cuts of the intertransverse L4-L5 grafting location were rated blindly for nerve root impingement, and degree of cord impingement and rated for the presence of bone, bone bridging, and fusion.

Quantitative analysis included determination of volume of new bone formation and mean bone mineral density via computer analysis. CT cuts were scanned with a photomicrodensitometer to estimate the volume of bone of the fusion mass.

The lumbar spinal segment L4-L5 was qualitatively evaluated via manual bending performed by the surgeon. The evaluation involves the slight bending of the L4-L5 level and examination of the any relative motion between L4 and L5 on both left and right sides.

| Condition + BMP dose | manual fusions | imaging fusions | mechanical stiffness | | |
|---|---|---|---|---|---|
| | | | sagittal | coronal | axial |
| Decorticated | | | | | |
| 920 µg | 3/3 | 3/3 | 149 ± 00 | 131 ± 00 | 2.0 ± 00 |
| 230 µg | 4/4 | 4/4 | 212 ± 30 | 248 ± 41 | 3.5 ± 0.5 |
| 58 µg | 4/4 | 3/4 | 181 ± 91 | 139 ± 110 | 3.3 ± 1.5 |
| average Undecorticated | | | | | |
| 920 µg | 3/3 | 3/3 | 155 ± 28 | 236 ± 06 | 3.8 ± 0.3 |
| 230 µg | 3/3 | 3/3 | 150 ± 26 | 335 ± 47 | 3.2 ± 0.7 |
| 58 µg | 2/3 | 1/3 | 133 ± 84 | 134 ± 37 | 2.7 ± 0.5 |
| average | 8/9 | 7/9 | 146 | 235 | 3.2 |

Only the presence of complete bilateral transverse process osseous union was considered successful radiographic fusion. 100% of decorticated specimens implanted with rhBMP-2/OPLA exhibited gross fusion by manual manipulation compared to 89% of undecorticated specimens (p=n·s). 91% of these were graded radiographic successes compared to 78% of undecorticated specimens (p=n·s). All failures were associated with the 58 pg dose of BMP. There were no overall differences in mechanical stiffness between the two groups. When the 58 μg specimens were excluded there was greater stiffness to coronal bending in the undecorticated specimens ($p<0.05$). However, coronal bending stiffness was more correlated to BMP dose than to the condition of host cortex ($p<0.03$).

Conclusion: There were no statistical differences in clinical and radiographic fusion rates between decorticated and undecorticated sites. Mechanical fusion characteristics were similar in both groups. The dose of rhBMP-2 delivered was a better predictor for successful fusion than was host bed preparerion.

EXAMPLE 2

Collagen Carrier

A rhBMP-2/absorbably collagen implant is prepared from Helistat® Absorbably Collagen Hemostatic Agent (Integra LiteSciences Corporation) and rhBMP-2. The implant is evaluated and compared to the rhBMP-2/OPLA implant according to the methods described in Example 1.

EXAMPLE 3

PMMA Carrier

A rhBMP-2/PMMA implant is prepared from admixing rhBMP-2 and polymethylmethacrylate. The implant is evaluated and compared to the rhBMP-2/OPLA implant according to the methods described in Example 1.

What is claimed is:

1. A surgical procedure for stabilizing, vertebrae in a spine, comprising the steps of:

exposing cortical bone of a portion of each of adjacent vertebrae each said portion being outside an intervertebral disc space between the adjacent vertebrae; and placing an osteoinductive material within an area between the portions of the adjacent vertebrae in contact with only the cortical bone of the portions.

2. The surgical procedure of claim 1 wherein said placing step includes placing strips containing the osteoinductive material within the area between the portions.

3. The surgical procedure of claim 1 wherein said portions are at a posterior aspect of the spine.

4. The surgical procedure of claim 1 wherein said portions are the transverse processes of the adjacent vertebrae.

5. The surgical procedure of claim 1 wherein said portions are the adjacent vertebral endplates of the adjacent vertebrae.

6. The surgical procedure of claim 1 wherein said osteoinductive material includes an osteoinductive cytokine.

7. The surgical procedure of claim 1 wherein said placing step includes placing sheets containing the osteoinductive material within the area between the portions.

8. The surgical procedure of claim 1 wherein said placing step includes placing an implant containing said osteoinductive material within the area between the portions.

9. The surgical procedure of claim 3 wherein said portions are the spinous processes of the adjacent vertebrae.

10. The surgical procedure of claim 3 wherein said portions are within the neural arch of each of the adjacent vertebrae.

11. The surgical procedure of claim 6 wherein said osteoinductive material includes a bone morphogenic protein.

12. The surgical procedure of claim 6 wherein said osteoinductive material further includes a carrier selected from the group consisting of calcium sulfate, polylactic acids, polyanhydrides, collagen, calcium phosphate ceramics and polymeric acrylic esters.

13. The surgical procedure of claim 11 wherein said bone morphogenic protein is selected from the group consisting of BMP-1, BMP-2, BMP-3, BMP-4, BMP-5, BMP-6, BMP-6, BMP-7, BMP-8, BMP-9, BMP-10, and BMP-11.

14. The surgical procedure of claim 13 wherein said bone morphogenic protein is BMP-2.

15. The surgical procedure of claim 12 wherein said carrier is an open-porosity polylactic acid polymer.

16. The surgical procedure of claim 12 wherein said carrier includes tricalcium phosphate.

17. The surgical procedure of claim 16 wherein said carrier is a biphasic tricalcium phosphate/hydroxyapatite ceramic.

18. The surgical procedure of claim 12 wherein said carrier includes collagen.

19. The surgical procedure of claim 18 wherein said carrier is fibrillar collagen.

20. The surgical procedure of claim 19 wherein said osteoinductive material is an admixture of the osteoinductive cytokine and a polymeric acrylic ester carrier.

21. The surgical procedure of claim 20 wherein the polymeric acrylic ester is polymethylmethacrylate.

22. A surgical procedure for stabilizing a spine, comprising the steps of:

exposing cortical bone of a portion of each of adjacent vertebrae in the spine; and injecting an osteoinductive material into the disc space between the adjacent vertebrae and in contact with only the cortical bone of the portions.

23. A surgical procedure for stabilizing a spine, comprising the steps of:

exposing cortical bone of a portion of each of adjacent vertebrae each said portion being outside an intervertebral disc space between the adjacent vertebrae;

adding an osteoinductive cytokine to a carrier material; and placing the carrier material between said portions of the adjacent vertebrae in contact with only the nondecorticated bone of the portions.

24. The surgical procedure of claim 23 wherein said adding step includes injecting said cytokine into said carrier material before said placing step.

25. The surgical procedure of claim 23 wherein said adding step includes injecting said cytokine into said carrier material after said placing step.

26. The surgical procedure of claim 23 wherein said portions are the transverse processes of the adjacent vertebrae.

27. The surgical procedure of claim 23 wherein said osteoinductive cytokine includes a bone morphogenic protein.

28. The surgical procedure of claim 27 wherein said bone morphogenic protein is selected from the group consisting of BMP-1, BMP-2, BMP-3, BMP-4, BMP-5, BMP-6, BMP-6, BMP-7, BMP-8, BMP-9, BMP-10, and BMP-11.

* * * * *